(12) United States Patent
Li et al.

(10) Patent No.: US 11,370,732 B2
(45) Date of Patent: Jun. 28, 2022

(54) METHOD OF SEPARATING α-OLEFIN BY A SIMULATED MOVING BED

(71) Applicant: Inner Mongolia Yitai Coal-based New Materials Research Institute Co., Ltd., Erdos (CN)

(72) Inventors: Juncheng Li, Erdos (CN); Zhen Qian, Erdos (CN); Jingwei Wu, Erdos (CN); Xiaolong Zhang, Erdos (CN); Qinge Jian, Erdos (CN); Yuan Gao, Erdos (CN); Xueting Wu, Erdos (CN); Haoting Chen, Erdos (CN)

(73) Assignee: INNER MONGOLIA YITAI COAL-BASED NEW MATERIALS RESEARCH INSTITUTE CO., LTD., Erdos (CN)

( * ) Notice: Subject to any disclaimer, the term of this patent is extended or adjusted under 35 U.S.C. 154(b) by 0 days.

(21) Appl. No.: 17/288,395

(22) PCT Filed: Jun. 14, 2019

(86) PCT No.: PCT/CN2019/091271
§ 371 (c)(1),
(2) Date: Apr. 23, 2021

(87) PCT Pub. No.: WO2020/177235
PCT Pub. Date: Sep. 10, 2020

(65) Prior Publication Data
US 2021/0380505 A1     Dec. 9, 2021

(30) Foreign Application Priority Data

Mar. 4, 2019   (CN) .......................... 201910196902.X

(51) Int. Cl.
*C07C 7/13*     (2006.01)
*B01D 15/02*    (2006.01)
(Continued)

(52) U.S. Cl.
CPC ................ *C07C 7/13* (2013.01); *B01D 15/02* (2013.01); *B01D 15/12* (2013.01);
(Continued)

(58) Field of Classification Search
None
See application file for complete search history.

(56) References Cited

U.S. PATENT DOCUMENTS

| 3,510,423 A | 5/1970 | Neuzil et al. |
| 4,455,445 A * | 6/1984 | Neuzil .................... C07C 7/13 95/143 |

(Continued)

FOREIGN PATENT DOCUMENTS

| CN | 101462919 A | 6/2009 |
| CN | 102452888 A | 5/2012 |

(Continued)

OTHER PUBLICATIONS

Chemical Encyclopedia, vol. 3, p. 1 637, 1993 with English translation (5 pages).

(Continued)

*Primary Examiner* — Ali Z Fadhel
(74) *Attorney, Agent, or Firm* — Osha Bergman Watanabe & Burton LLP

(57) ABSTRACT

The present disclosure provides a method of separating α-olefin by a simulated moving bed. The method comprises using a coal-based Fischer-Tropsch synthetic oil as a raw material to obtain a target olefin having a carbon number N within a range from 9 to 18, wherein the raw material is subjected to treatment steps including pretreatment, fraction cutting, alkane-alkene separation, and isomer separation, thereby obtaining a high purity α-olefin product. As compared to conventional rectification and extraction processes, the product obtained by the method of the present disclosure (Continued)

has advantages of higher purity, higher yield, lower energy consumption, and significantly reduced production cost.

19 Claims, 1 Drawing Sheet

(51) Int. Cl.
*B01D 15/12* (2006.01)
*B01D 15/18* (2006.01)
*B01J 20/18* (2006.01)
*C07C 7/00* (2006.01)
*C07C 7/04* (2006.01)

(52) U.S. Cl.
CPC .......... *B01D 15/1864* (2013.01); *B01J 20/18* (2013.01); *C07C 7/005* (2013.01); *C07C 7/04* (2013.01); *B01D 2257/7022* (2013.01); *C07B 2200/07* (2013.01)

(56) References Cited

U.S. PATENT DOCUMENTS

| | | | |
|---|---|---|---|
| 4,567,309 A * | 1/1986 | Kulprathipanja | C07C 7/13 585/829 |
| 5,132,485 A * | 7/1992 | Ou | C07C 7/13 585/820 |
| 5,220,102 A * | 6/1993 | Funk | C07C 7/13 585/820 |
| 6,407,305 B1 * | 6/2002 | Sohn | C07C 7/005 585/820 |
| 7,217,852 B1 | 5/2007 | DeHaan et al. | |
| 7,294,253 B2 | 11/2007 | DeHaan et al. | |
| 2015/0148576 A1 * | 5/2015 | Kulprathipanja | C07C 2/64 585/448 |
| 2015/0148577 A1 * | 5/2015 | Kulprathipanja | C07C 2/64 585/448 |
| 2016/0046545 A1 | 2/2016 | Maher | |
| 2017/0022125 A1 * | 1/2017 | Fichtl | C07C 4/02 |
| 2020/0172454 A1 * | 6/2020 | Xing | B01J 20/22 |

FOREIGN PATENT DOCUMENTS

| | | |
|---|---|---|
| CN | 104370678 A | 2/2015 |
| CN | 105777467 A | 7/2016 |
| CN | 109503307 A | 3/2019 |
| EP | 1835011 A1 | 9/2007 |

OTHER PUBLICATIONS

Office Action issued in corresponding CN Application No. 201910196902.X with English translation dated Feb. 2, 2021 (17 pages).
International Search Report issued in International Application No. PCT/CN2019/091271 dated Dec. 4, 2019 (2 pages).
Written Opinion issued in International Application No. PCT/CN2019/091271 dated Dec. 4, 2019 (6 pages).

* cited by examiner

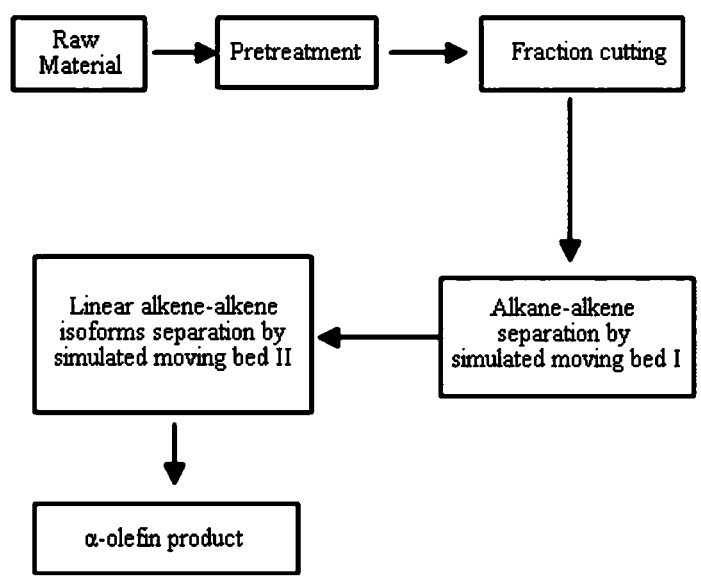

METHOD OF SEPARATING α-OLEFIN BY A SIMULATED MOVING BED

TECHNICAL FIELD

The present disclosure relates to a method of separating α-olefin by a simulated moving bed, and particularly to a method of separating high purity α-olefin from a coal-based Fischer-Tropsch synthetic oil through two stages of simulated moving beds.

BACKGROUND

Fischer-Tropsch synthetic oil products contain a large amount of valuable chemical raw materials such as olefins. Olefins are key raw materials for producing other fine chemicals, and greatly influence the downstream industries. Currently, the domestic and abroad subsequent processing methods for Fischer-Tropsch synthetic oil products mainly focus on distillation and rectification.

U.S. Pat. Nos. 7,217,852 and 7,294,253 provide a method for distilling a Fischer-Tropsch synthetic oil product and middle distillates obtained from the distillation. The middle distillates contain branches such as methyl, ethyl and propyl groups, and C9-C16 components account for 90% or more of the total distillates. The middle distillates are main components of diesel, and have good low temperature fluidity. However, the product obtained by this method has a low purity, and cannot be directly used for a polymerization reaction.

EP Publication No. 1835011 provides a method of distilling a Fischer-Tropsch synthetic crude product and middle distillates obtained therefrom. The main process includes fractionating (fraction cutting) the FTS crude product into naphtha and middle distillates. SASOL Company, South Africa developed a combined process of "alkali washing-etherification-rectification-extraction" in 1994, enabling the preparation of polymerization grade 1-hexene and 1-octene. However, this process route is relatively complex and has a high energy consumption, resulting in very high capital and operating costs. And this technology can only separate C6 and C8 components, and it cannot separate components with higher carbon numbers.

In CN Publication No. 104370678, a high temperature Fischer-Tropsch synthetic C5 light distillate is used as a raw material. The raw material is subjected to an extractive rectification, wherein the extractant is N,N-dimethyl formamide, and the 1-pentene enriched material obtained from the overhead of the extractive rectification column is further purified by a precise rectification to obtain an 1-pentene product. This method only obtains the product having single carbon number, and the basis method as used is extractive rectification, which has a high energy consumption and large solvent consumption, resulting in a high production cost.

A simulated moving bed is a separation device for performing separation operations by means of the adsorption principle. The simulated moving bed technology, as a main representative for the continuous chromatography, has advantages of high production efficiency, low organic solvent consumption, large mass transfer force, convenient automated continuous production, and so on, and thus is widely applied in various fields such as petrochemical industry, food industry and pharmaceutical industry. The simulated moving bed process is a complex industrial process and is a non-linear, unequilibrated, non-ideal, and multivariant periodic process influenced by numerous factors.

All of the separation processes in the above technical literatures utilize a conventional extractive rectification process. Since the difference in the boiling point between α-olefins and impurites (isomerized olefins) is very slight, the cost for separation using the extractive rectification process is very high, and the solvent has a large consumption and is difficult to be recovered, failing to meeting the demand for current social development. Although current technologies can separate liquid alkenes and liquid alkanes, there is still a need for providing a further modified method for separating alkenes from alkanes.

In view of the above drawbacks, the inventors of the present application firstly propose a method of efficiently and economically separating α-olefins with a wide range of carbon chains from a raw material of Fischer-Tropsch synthetic oil by combining the raw material of Fischer-Tropsch synthetic oil with two stages separation using simulated moving beds. The method breaks through the conventional route of separating α-olefins with a specific carbon number or with a narrow range of carbon chains through extractive rectification.

SUMMARY

The technical problem to be solved by the present disclosure is to efficiently and economically separate α-olefin from a coal-based Fischer-Tropsch synthetic oil to obtain an olefin product satisfying the purity demand. In particular, the present disclosure provides an α-olefin separation method with simple process and low energy consumption, which can meet various purity and carbon number distribution requirements (for example, C4-C18) for olefins in the market.

In order to achieve the object of the present disclosure, the technical solutions used are as follows.

A method of separating α-olefin by a simulated moving bed, wherein a coal-based Fischer-Tropsch synthetic oil is used as a raw material, and a target olefin has a carbon number N within a range from 4 to 18, the method comprising steps of:

(1) fraction cutting: subjecting a pretreated raw material to fraction cutting, to obtain a component having a carbon number of N;

(2) alkane-alkene separation: subjecting the component obtained in step (1) to an alkane-alkene separation using a first simulated moving bed to separate alkanes and alkenes, thereby obtaining an olefin-rich component; and (3) isomer separation: subjecting the olefin-rich component obtained in step (2) to an isomer separation using a second simulated moving bed, to separate a high purity α-olefin product.

In some embodiments, the method does not comprise a step of removing an oxygen-containing compound before the step of alkane-alkene separation.

In some embodiments, the first simulated moving bed in step (2) has process parameters as follows: an operating temperature of 50-110° C., an operating pressure of 0.3-0.8 MPa, and a mass ratio of adsorbent to synthetic oil of 0.5-4:1; preferably, an operating temperature of 60-100° C., an operating pressure of 0.4-0.6 MPa, and a mass ratio of adsorbent to synthetic oil of 0.5-2:1.

In some embodiments, the second simulated moving bed in step (3) has process parameters as follows: an operating temperature of 50-110° C., an operating pressure of 0.3-0.8 MPa, and a mass ratio of adsorbent to synthetic oil of 0.5-4:1; preferably, an operating temperature of 60-100° C., an operating pressure of 0.4-0.6 MPa, and a mass ratio of adsorbent to synthetic oil of 0.5-2:1.

In some embodiments, an adsorbent in the first simulated moving bed is a Series A molecular sieve, preferably 5A molecular sieve and/or modified 5A molecular sieve.

In some embodiments, an adsorbent in the second simulated moving bed is a Series X molecular sieve, preferably 13X molecular sieve and/or modified 13X molecular sieve.

In some embodiments, the target olefin preferably has a carbon number N within a range from 9 to 18, preferably from 9 to 16, more preferably from 10 to 14, and further preferably from 10 to 12.

In some embodiments, the coal-based Fischer-Tropsch synthetic oil has an alkene content of 73-75 wt %, an alkane content of 22-25 wt %, and an oxygen-containing compound content of 3-5 wt %.

In some embodiments, the pretreatment step comprises a step of deacidifying the raw material.

In some embodiments, both the first and second simulated moving beds comprise an adsorption bed, a raw material feeding system, a desorbent feeding system, a circulation system, an extract liquid system, a raffinate system, a program-controlled valve group and an automatic control system; wherein the adsorption bed comprises a plurality of adsorption columns, and is divided into an adsorption area, a purification area, a desorption area and a buffering area;

each of the adsorption columns is provided with a raw material feed valve, a desorbent feed valve, and a circulating fluid feed valve at a top end;

each of the adsorption columns is provided with a raffinate discharge valve and a extract liquid discharge valve at a bottom end;

a check valve is provided between two adjacent adsorption columns;

the raw material feeding system is connected to the raw material feed valve of each of the adsorption columns;

the desorbent feeding system is connected to the desorbent feed valve of each of the adsorption columns;

the circulation system comprises a circulation pump, and is connected to the circulating fluid feed valve of each of the adsorption columns via the circulation pump;

the extract liquid system is connected to the extract liquid discharge valve of each of the adsorption columns;

the raffinate system is connected to the raffinate discharge valve of each of the adsorption columns;

all of the valves form the program-controlled valve group, and the program-controlled valve group is connected to the automatic control system which is capable of controlling open and close states of each valve of the program-controlled valve group.

In some embodiments, the high purity α-olefin product has an α-olefin content of 99.2 wt % or more.

As compared to prior art, the present disclosure has the following advantageous effects.

1. In a mixture of alkanes and alkenes, the alkenes are polar substances, and the alkanes are non-polar or weakly polar substances. Thus, the alkenes and the alkanes have different adsorption performances on a certain adsorbent due to their different polarities. In the method of the present invention, the mixed components are separated from each other by making use of difference in adsorption performance between different substances, rather than through conventional rectification and extraction processes which make use of difference in boiling point. As compared to conventional rectification and extraction processes, in the present invention, simulated moving beds in series are used for performing separation, and the α-olefin product obtained has advantages of higher purity, higher yield, lower energy consumption, and reduced production cost which is about 15% of the production cost for a convention process.

2. The method of the present disclosure is particularly suitable for the process of separating α-olefin from a coal-based Fischer-Tropsch synthetic oil. The combination of various process parameters is closely related to the composition of the raw material, and is obtained by a continuous adjustment and improvement process from a lab scale test to a pilot scale test through analysis of raw materials and adjustment of parameters.

3. Depending on the demand in the market, in the method of the present invention, no step of removing oxygen-containing compound is provided after the fraction cutting step, in order to reduce production cost. Although the presence of a small amount of oxygen-containing compound will lead to reduced lifetime of the adsorbent in the simulated moving bed and increased ratio of adsorbent to oil, the overall product cost can be reduced as compared to a method comprising a step of removing oxygen-containing compound, and a high purity α-olefin product as desired can be obtained.

4. In the present invention, a program-controlled valve group is used in place of a conventional multichannel rotary valve to control periodic switch of the simulated moving bed, reducing the manufacture cost of the device. The program-controlled valve group can be flexibly taken out according to maintenance requirements, which is convenient for device maintenance. Each adsorption column can be taken out for maintenance, and put back into the system after the replacement of adsorbent. As a result, the long term operation capability of the device is greatly improved.

BRIEF DESCRIPTION OF DRAWINGS

FIG. 1 is a schematic diagram of the method of separating α-olefin by a simulated moving bed according to the present invention.

DETAILED DESCRIPTION

The process flow of the present disclosure is as shown in FIG. 1, wherein the raw material is subjected to a pretreatment, a fraction cutting, an alkane-alkene separation with simulated moving bed I, and a linear alkene-alkene isoforms separation with simulated moving bed II to obtain an α-olefin product.

After the raw material is subjected to a deacidification pretreatment, the distillate is fed into a light component removal column to separate components with a carbon number less than N from the overhead of the light component removal column, and the bottom components are fed into a heavy component removal column. In the heavy component removal column, components with a carbon number greater than N are separated from the bottom of the heavy component removal column, and a component with a carbon number of N is separated from the overhead of the heavy component removal column. After fraction cutting, the oxygen-containing compound content in the distillate is further reduced.

In the simulated moving bed, the fixed adsorbent bed is divided into a plurality of sections, wherein the sections are charged with an adsorbent and inter-section liquids cannot be in fluid communication with each other directly. Each section is provided with inlet/outlet pipe(s), and the inflow/outflow is controlled by a valve. Typically, in a simulated moving bed having 8 adsorption columns, 20 inlets/outlets, among total 24 inlets/outlets, only serve for inter-section communication, and the other 4 inlets/outlets serve for the inflow or outflow of four material streams. At a certain moment, depending on the inlets/outlet positions of streams, the whole adsorption bed is divided into four areas with different lengths and different interphase mass transfer from each other. The four inlets/outlets for streams in the simulated moving bed move upwards at a speed synchronized with the change of solid phase concentration, thereby forming a closed loop. The overall result is substantially the same as the case where the solid adsorbent moves from top to bottom in an adsorber with the positions of the inlets/outlets kept unchanged, thereby achieving the separation effect.

The operating parameters for the simulated moving bed are as follows.

The first simulated moving bed: 50-110° C., an operating pressure of 0.3-0.8 MPa, a simulated moving bed adsorbent of Series A molecular sieve (for example, 3A, 4A, 5A or modified 5A molecular sieve), and a mass ratio of adsorbent to synthetic oil of 0.5-4:1. The content of olefin component obtained is 99.5 wt % or more.

The second simulated moving bed: 50-110° C., an operating pressure of 0.3-0.8 MPa, a simulated moving bed adsorbent of Series X molecular sieve (for example, 13X or modified 13X molecular sieve), and a mass ratio of adsorbent to synthetic oil of 0.5-4:1. The content of α-olefin component obtained is 99.6 wt % or more.

The distillate raw material used in the present disclosure is sourced from the coal-to-oil plant (1.2 million tons per year) from Yitai Chemical Industry Co. Ltd., Inner Mogolia, and the composition thereof is as shown in Table 1.

TABLE 1

The raw material components of the distillate

| No. | Material type | Content/wt % |
|---|---|---|
| 1 | Alkanes (n-alkane/alkane isoforms) | 23.17 |
| 2 | Alkenes (n-alkene/alkene isoforms) | 71.83 |
| 3 | Acids | 0.5 |
| 4 | Alcohols | 4 |
| 5 | Aldehydes, esters and ketones | 0.5 |

The raw material components in the deacidified distillate are as shown in Table 2.

TABLE 2

The composition of the deacidified distillate

| No. | Material type | Content/wt % |
|---|---|---|
| 1 | Alkanes (n-alkane/alkane isoforms) | 23.90 |
| 2 | Alkenes (n-alkene/alkene isoforms) | 74.10 |
| 3 | Acids | — |
| 4 | Aldehydes, esters and ketones | 2 |

The raw material components in the distillate after fraction cutting are as shown in Table 3.

TABLE 3

The composition of the distillate after fraction cutting

| No. | Material type | Content/wt % |
|---|---|---|
| 1 | Alkanes (n-alkane/alkane isoforms) | 24.40 |
| 2 | Alkenes (n-alkene/alkene isoforms) | 75.40 |
| 3 | Acids | — |
| 4 | Aldehydes, esters and ketones | 0.2 |

Comparative Example 1

The target carbon number is 9. The raw material was pretreated, subjected to fraction cutting, and then subjected to an alkane-alkene separation by extractive rectification, without separation by a simulated moving bed. Here, for the alkane-alkene separation, the operating temperature was 100-105° C., the overhead temperature was 48-50° C., the reflux ratio was 5, the ratio of agent to oil (a mass ratio of adsorbent to synthetic oil) was 1:1, the extractant was NMP (referring to the 4th extractant in Example 1 of CN 105777467A), and the content of olefin component obtained was 98.08 wt %. No linear hydrocarbon-branched hydrocarbon separation was performed, since the difference in boiling point between the linear hydrocarbon and the branched hydrocarbon was only 3° C., and thus it was very difficult to separate them from each other by a rectification process.

Examples 1-10

In the treatment methods of Examples 1-10, the pretreatment and fraction cutting steps were the same as those in Comparative Example 1, but the fractions obtained after fraction cutting were fed to a first simulated moving bed for an alkane-alkene separation, and the separated olefin-rich product was fed to a second simulated moving bed for an isomer separation. Specific operating parameters are shown in Table 5. As seen from Table 5, the α-olefin obtained from separation by a simulated moving bed had a purity of not less than 99.2 wt %, and an oxygen-containing compound content of less than 50 ppm.

TABLE 5

The carbon numbers of target α-olefins and the process parameters for Examples 1-10

| No. | Target carbon number | Operating parameters for simulated moving bed I | Olefin content in olefin-rich component | Operating parameters for simulated moving bed II | Purity of final product | Content of oxygen-containing compound |
|---|---|---|---|---|---|---|
| Ex. 1 | 9 | 60° C., 0.5 MPa, Adsorbent: 4A molecular sieve, Adsorbent to oil mass ratio: 3.5:1 | 99.0 wt % | 62° C., 0.52 MPa, Adsorbent: 10x molecular sieve, Adsorbent to oil mass ratio: 2.5:1 | 99.3 wt % | <50 ppm |

TABLE 5-continued

The carbon numbers of target α-olefins and the process parameters for Examples 1-10

| No. | Target carbon number | Operating parameters for simulated moving bed I | Olefin content in olefin-rich component | Operating parameters for simulated moving bed II | Purity of final product | Content of oxygen-containing compound |
|---|---|---|---|---|---|---|
| Ex. 2 | 10 | 67° C., 0.52 MPa, Adsorbent: 5A molecular sieve, Adsorbent to oil mass ratio: 1.5:1 | 99.1 wt % | 67° C., 0.54 MPa, Adsorbent: 13x molecular sieve, Adsorbent to oil mass ratio: 2:1 | 99.3 wt % | <50 ppm |
| Ex. 3 | 11 | 70° C., 0.6 MPa, Adsorbent: 5A molecular sieve, Adsorbent to oil mass ratio: 3:1 | 99.2 wt % | 73° C., 0.57 MPa, Adsorbent: 13x molecular sieve, Adsorbent to oil mass ratio: 2.5:1 | 99.5 wt % | <50 ppm |
| Ex. 4 | 12 | 73° C., 0.5 MPa, Adsorbent: 5A molecular sieve, Adsorbent to oil mass ratio: 1.8:1 | 99.1 wt % | 70° C., 0.5 MPa, Adsorbent: 13x molecular sieve, Adsorbent to oil mass ratio: 2:1 | 99.4 wt % | <50 ppm |
| Ex. 5 | 13 | 88° C., 0.57 MPa, Adsorbent: 5A molecular sieve, Adsorbent to oil mass ratio: 2.5:1 | 99.1 wt % | 85° C., 0.59 MPa, Adsorbent: 13x molecular sieve, Adsorbent to oil mass ratio: 2.5:1 | 99.3 wt % | <50 ppm |
| Ex. 6 | 14 | 91° C., 0.55 MPa, Adsorbent: 5A molecular sieve, Adsorbent to oil mass ratio: 1.6:1 | 99.0 wt % | 90° C., 0.52 MPa, Adsorbent: 13x molecular sieve, Adsorbent to oil mass ratio: 1.5:1 | 99.2 wt % | <50 ppm |
| Ex. 7 | 15 | 96° C., 0.52 MPa, Adsorbent: 5A molecular sieve, Adsorbent to oil mass ratio: 1.5:1 | 99.0 wt % | 98° C., 0.57 MPa, Adsorbent: 13x molecular sieve, Adsorbent to oil mass ratio: 1.8:1 | 99.2 wt % | <50 ppm |
| Ex. 8 | 16 | 100° C., 0.6 MPa, Adsorbent: 5A molecular sieve, Adsorbent to oil mass ratio: 2:1 | 99.1 wt % | 102° C., 0.66 MPa, Adsorbent: 13x molecular sieve, Adsorbent to oil mass ratio: 2:1 | 99.3 wt % | <50 ppm |
| Ex. 9 | 17 | 105° C., 0.67 MPa, Adsorbent: 5A molecular sieve, Adsorbent to oil mass ratio: 2:1 | 99.2 wt % | 103° C., 0.72 MPa, Adsorbent: 13x molecular sieve, Adsorbent to oil mass ratio: 2.4:1 | 99.3 wt % | <50 ppm |
| Ex. 10 | 18 | 110° C., 0.73 MPa, Adsorbent: 5A molecular sieve, Adsorbent to oil mass ratio: 2:1 | 99.2 wt % | 106° C., 0.7 MPa, Adsorbent: 13x molecular sieve, Adsorbent to oil mass ratio: 1.6:1 | 99.4 wt % | <50 ppm |

The invention claimed is:

1. A method of separating α-olefin by a simulated moving bed, wherein a coal-based Fischer-Tropsch synthetic oil is used as a raw material, and a target olefin has a carbon number N within a range from 4 to 18, the method comprising steps of:
   (1) fraction cutting: subjecting a pretreated raw material to fraction cutting, to obtain a component having a carbon number of N;
   (2) alkane-alkene separation: subjecting the component obtained in step (1) to an alkane-alkene separation using a first simulated moving bed, to separate alkanes and alkenes, thereby obtaining an olefin-rich component; and
   (3) isomer separation: subjecting the olefin-rich component obtained in step (2) to an isomer separation using a second simulated moving bed, to separate a α-olefin-rich product.

2. The method of separating α-olefin by a simulated moving bed according to claim 1, wherein the first simulated moving bed in step (2) has process parameters as follows:
   an operating temperature of 50-110° C., an operating pressure of 0.3-0.8 MPa, and a mass ratio of adsorbent to synthetic oil of 0.5-4:1.

3. The method of separating α-olefin by a simulated moving bed according to claim 1, wherein the second simulated moving bed in step (3) has process parameters as follows:
   an operating temperature of 50-110° C., an operating pressure of 0.3-0.8 MPa, and a mass ratio of adsorbent to synthetic oil of 0.5-4:1.

4. The method of separating α-olefin by a simulated moving bed according to claim 1, wherein the adsorbent in the first simulated moving bed is a Series A molecular sieve.

5. The method of separating α-olefin by a simulated moving bed according to claim 4, wherein the Series A molecular sieve is 5A molecular sieve or modified 5A molecular sieve.

6. The method of separating α-olefin by a simulated moving bed according to claim 1, wherein the adsorbent in the second simulated moving bed is a Series X molecular sieve.

7. The method of separating α-olefin by a simulated moving bed according to claim 6, wherein the Series X molecular sieve is 13X molecular sieve or modified 13X molecular sieve.

8. The method of separating α-olefin by a simulated moving bed according to claim 1, wherein the target olefin has a carbon number N within a range from 9 to 18.

9. The method of separating α-olefin by a simulated moving bed according to claim 8, wherein the target olefin has a carbon number N within a range from 9 to 16.

10. The method of separating α-olefin by a simulated moving bed according to claim 9, wherein the target olefin has a carbon number N within a range from 10 to 14.

11. The method of separating α-olefin by a simulated moving bed according to claim 10, wherein the target olefin has a carbon number N within a range from 10 to 12.

12. The method of separating α-olefin by a simulated moving bed according to claim 1, wherein the coal-based Fischer-Tropsch synthetic oil has an alkene content of 73-75 wt %, an alkane content of 22-25 wt %, and an oxygen-containing compound content of 3-5 wt %.

13. The method of separating α-olefin by a simulated moving bed according to claim 1, wherein the pretreatment step comprises a step of deacidifying the raw material.

14. The method of separating α-olefin by a simulated moving bed according to claim 13, wherein after the raw material is subjected to a deacidification pretreatment, the distillate is fed into a light component removal column to separate components with a carbon number less than N from the overhead of the light component removal column, and the bottom components are fed into a heavy component removal column; and in the heavy component removal column, components with a carbon number greater than N are separated from the bottom of the heavy component removal column, and a component with a carbon number of N is separated from the overhead of the heavy component removal column.

15. The method of separating α-olefin by a simulated moving bed according to claim 1, wherein both the first and second simulated moving beds comprise an adsorption bed, a raw material feeding system, a desorbent feeding system, a circulation system, an extract liquid system, a raffinate system, a program-controlled valve group and an automatic control system; wherein the adsorption bed comprises a plurality of adsorption columns and is divided into an adsorption area, a purification area, a desorption area and a buffering area;

each of the adsorption columns is provided with a raw material feed valve, a desorbent feed valve, and a circulating fluid feed valve at a top end;

each of the adsorption columns is provided with a raffinate discharge valve and a extract liquid discharge valve at a bottom end;

a check valve is provided between two adjacent adsorption columns;

the raw material feeding system is connected to the raw material feed valve of each of the adsorption columns;

the desorbent feeding system is connected to the desorbent feed valve of each of the adsorption columns;

the circulation system comprises a circulation pump, and is connected to the circulating fluid feed valve of each of the adsorption columns via the circulation pump;

the extract liquid system is connected to the extract liquid discharge valve of each of the adsorption columns;

the raffinate system is connected to the raffinate discharge valve of each of the adsorption columns;

all of the valves form the program-controlled valve group, and the program-controlled valve group is connected to the automatic control system which is capable of controlling open and close states of each valve of the program-controlled valve group.

16. The method of separating α-olefin by a simulated moving bed according to claim 1, wherein the α-olefin-rich product has an α-olefin content of 99.2 wt % or more.

17. The method of separating α-olefin by a simulated moving bed according to claim 1, wherein the method does not comprise a step of removing oxygen-containing compound before the step of alkane-alkene separation.

18. The method of separating α-olefin by a simulated moving bed according to claim 1, wherein the first simulated moving bed in step (2) has process parameters as follows: an operating temperature of 60-100° C., an operating pressure of 0.4-0.6 MPa, and a mass ratio of adsorbent to synthetic oil of 0.5-2:1.

19. The method of separating α-olefin by a simulated moving bed according to claim 1, wherein the second simulated moving bed in step (3) has process parameters as follows: an operating temperature of 60-100° C., an operating pressure of 0.4-0.6 MPa, and a mass ratio of adsorbent to synthetic oil of 0.5-2:1.

* * * * *